US010408891B2

(12) United States Patent
Fee et al.

(10) Patent No.: US 10,408,891 B2
(45) Date of Patent: Sep. 10, 2019

(54) APPARATUS FOR TESTING SAMPLE PROPERTIES IN A MAGNETIC FIELD

(71) Applicant: HTS-110 Limited, Gracefield, Lower Hutt (NZ)

(72) Inventors: Michael Graeme Fee, Wellington (NZ); Oliver John Dickie, Wellington (NZ)

(73) Assignee: Scott Technology NZ Limited, Kenmure, Dunedin (NZ)

( * ) Notice: Subject to any disclaimer, the term of this patent is extended or adjusted under 35 U.S.C. 154(b) by 451 days.

(21) Appl. No.: 14/906,113

(22) PCT Filed: Jul. 15, 2014

(86) PCT No.: PCT/NZ2014/000146
§ 371 (c)(1),
(2) Date: Jan. 19, 2016

(87) PCT Pub. No.: WO2015/009168
PCT Pub. Date: Jan. 22, 2015

(65) Prior Publication Data

US 2016/0195591 A1 Jul. 7, 2016

(30) Foreign Application Priority Data

Jul. 19, 2013 (NZ) ........................................ 613440

(51) Int. Cl.
*G01R 33/032* (2006.01)
*G01N 27/72* (2006.01)
(Continued)

(52) U.S. Cl.
CPC ......... *G01R 33/0325* (2013.01); *G01N 21/21* (2013.01); *G01N 27/72* (2013.01); *G01R 33/032* (2013.01); *G01R 33/1207* (2013.01)

(58) Field of Classification Search
CPC ............ G01R 33/0325; G01R 33/1207; G01R 33/032; G01N 27/72; G01N 21/21
See application file for complete search history.

(56) References Cited

U.S. PATENT DOCUMENTS 4,946,590 A * 8/1990 Hertzog .................. B03C 1/288 210/222
9,696,391 B2 * 7/2017 Huang ................ G01R 33/445
(Continued)

FOREIGN PATENT DOCUMENTS

WO WO 2002/068980 9/2002
WO WO 2009/022993 2/2009
WO WO 2011/155903 12/2011

OTHER PUBLICATIONS

International Search Report for International Application No. PCT/NZ2014/000146 dated Dec. 11, 2014 (3 pages).
(Continued)

*Primary Examiner* — Vinh P Nguyen
*Assistant Examiner* — Zannatul Ferdous
(74) *Attorney, Agent, or Firm* — Merchant & Gould P.C.

(57) ABSTRACT

A magnetic testing apparatus includes a magnet assembly with a sample path extending through the magnet assembly. The magnetic field produced by the magnet assembly defines a known, varying magnetic field profile along the sample path. A sample is moved along sample path such that the sample portion is subjected to a predetermined magnetic field ramp or magnetic field profile during a measurement period. A measurement arrangement is also provided to measure one or more properties of the sample during the measurement period, in order to test sample properties at a plurality of different magnetic fields. The apparatus may be particularly suited to magneto-optical measurements,
(Continued)

including Magneto-Optical Kerr Effect measurements. The apparatus may be used for testing of hard disk platters.

27 Claims, 14 Drawing Sheets

(51) Int. Cl.
*G01N 21/21* (2006.01)
*G01R 33/12* (2006.01)

(56) References Cited

U.S. PATENT DOCUMENTS

2010/0170017 A1* 7/2010 Heidmann ........... G01R 33/032 850/48
2011/0019957 A1* 1/2011 Alameh .................. G02F 1/095 385/6
2012/0092972 A1 4/2012 Taratorin et al.

OTHER PUBLICATIONS

International Preliminary Report on Patentability for International Application No. PCT/NZ2014/000146 dated Jan. 19, 2016, 9 pages.
Arora et al. "A mirror based polar magneto-optical Kerr effect spectroscopy arrangement", 2011, 6 pages, Review of Scientific Instruments.
Oakberg et al. "Magneto-Optic Kerr Effect", 2010, 6 pages, Hinds Instruments Inc., Hillsboro, OR.

* cited by examiner

M
0
H
0

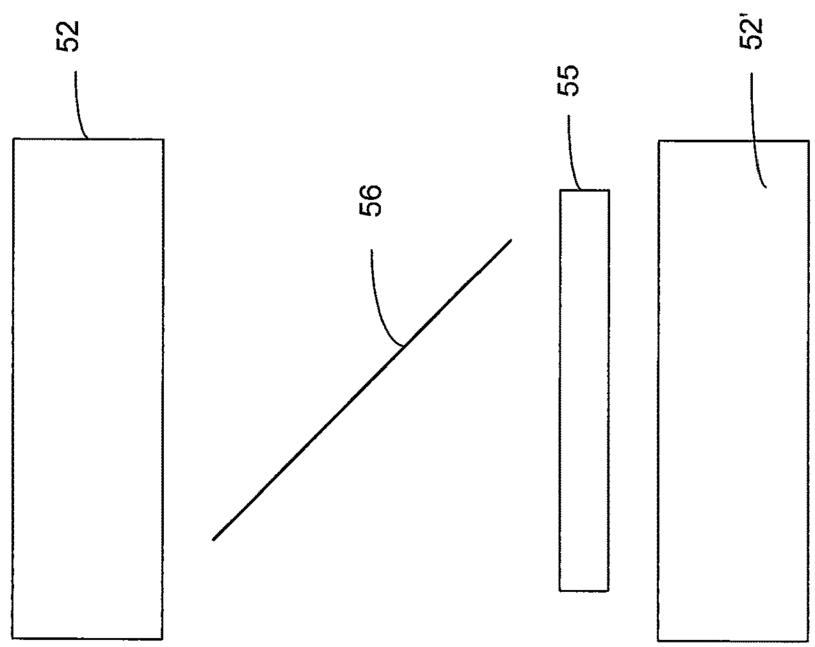
Figure 16
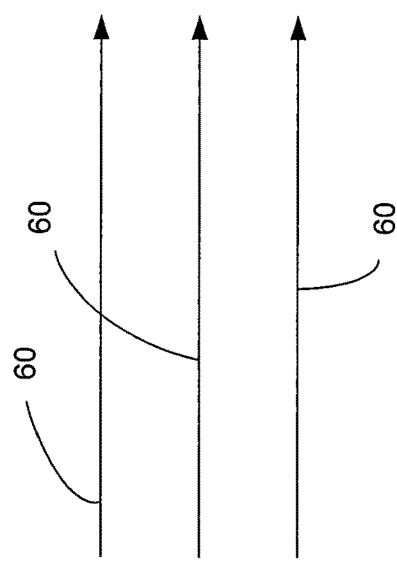

APPARATUS FOR TESTING SAMPLE PROPERTIES IN A MAGNETIC FIELD

This application is a National Stage Application of PCT/NZ2014/000146, filed 15 Jul. 2014, which claims benefit of Serial No. 613440, filed 19 Jul. 2013 in New Zealand and which applications are incorporated herein by reference. To the extent appropriate, a claim of priority is made to each of the above disclosed applications.

FIELD OF THE INVENTION

The invention relates to testing of samples, particularly but not exclusively to magneto-optical testing.

BACKGROUND TO THE INVENTION

Hard drive platters are formed from various magnetic materials applied to a substrate disc. Traditional hard drives use magnetic materials that can be read and written by a magnetic read/write head. However, other technologies have been suggested. In particular HAMR (Heat Assisted Magnetic Recording) materials use a thermally assisted write mechanism. This allows magnetic materials with relatively high coercivity to be used, with smaller bit sizes and higher storage density. In order to write to the disk, a laser beam is used to heat the magnetic material above the Curie temperature. The coercivity drops above this temperature, and a magnetic write field can be used to write data onto the disk. HAMR materials are a good candidate for future advances in hard drive technology.

In testing of hard drive platters, researchers probe the magnetic properties of the platter or a material sample using varying magnetic fields. In one method, a sample or platter is positioned in a magnetic field which can be ramped over time. As the field is ramped, Magneto-Optical Kerr Effect ("MOKE") measurements can be made. This involves introducing a polarised light beam onto the sample surface. The magnetized sample surface causes alterations in the polarisation and/or ellipticity of the reflected beam. The MOKE is well understood and need not be discussed in detail in this specification. However, a typical data set is illustrated in the graph of FIG. 1, where the vertical axis is magnetisation M, measured by MOKE techniques, and the horizontal axis is applied magnetic field H. This hysteresis loop is typical of magnetic materials used in hard drive platters.

In existing MOKE equipment, the polar Kerr effect is often used. This requires the magnetic field to be perpendicular to the sample surface and parallel to the plane of incidence. A typical apparatus is illustrated in FIG. 2. The apparatus includes a first magnetic pole 1 and second magnetic pole 2. Typically electromagnets are used, but the coils are not shown in FIG. 2. The first magnetic pole 1 has an aperture 3 to allow a polarised light beam 4 to be introduced. Generally the light beam is introduced perpendicular to the sample surface 5. In order not to influence the performance of the magnet, the aperture is generally just a few millimetres in diameter. The reflected laser beam 6 passes out through the same aperture and is separated from the incoming beam by a beam splitter 7. Various further optical components are also used, as will be understood by the skilled reader. In particular, a light source, light detector, polariser, analyser, modulator, lenses etc may be used as necessary for the particular application.

In order to measure the latest hard drive materials, higher magnetic fields are required. This leads to difficulties. While copper-wound electromagnets can be used up to fields of perhaps 3-5 tesla, higher fields require electromagnets wound with superconducting wire. Superconducting magnets are lossless in DC mode. However, when the magnetic field is ramped over time the superconducting coils produce heat. The required electrical ramping of the magnetic field over time therefore causes heat losses and inefficiency. At fast ramping rates, this would require additional cooling and more superconducting wire operating at lower current density. This would significantly raise costs. Further, the faster the ramping rate the higher the required voltage. Faster ramping requires high voltage power supplies that are not readily available in a form suitable for powering superconducting magnets.

These factors limit the speed at which the magnetic field can be ramped with acceptable performance, with a full four quadrant ramp (i.e. to define the full hysteresis loop of FIG. 1) taking about 1.5 to 5 minutes at 6-7 tesla. As the laser spot used is typically around 2-3 mm in diameter, it therefore takes several minutes to measure a very small area on the sample surface. Further, upgrading the speed capability of existing equipment would require either expensive new magnets or an expensive rebuild of the existing magnets.

In addition to the above problems, the ramping magnetic field creates time-varying fringe fields that can adversely affect any nearby equipment or experiments.

Arora et al (Arora, Ghosh and Sugunakar "*A mirror based polar magneto-optical Kerr effect spectroscopy arrangement*" Review of Scientific Instruments 82 123903 (2011)) suggest a polar MOKE apparatus in which a mirror is used to redirect the light beam onto a sample, such that an aperture in the magnet pole is not required. However, this system still suffers from the other drawbacks discussed above.

Reference to any prior art in this specification does not constitute an admission that such prior art forms part of the common general knowledge.

It is an object of the invention to provide a magneto-optical testing apparatus that addresses or at least ameliorates one or more of the above problems, or at least to provide the public with a useful choice.

SUMMARY OF THE INVENTION

In a first aspect the invention provides a magneto-optical hard disk platter testing apparatus, including: a magnet assembly; a sample path extending through the magnet assembly, a magnetic field produced by the magnet assembly defining a known, varying magnetic field profile along the sample path; a platter holder; a drive arrangement configured to cause relative movement between the magnet assembly and the platter holder, so as to move at least a sample portion of a platter held, in use, by the platter holder along the sampling path to subject the sample portion to at least part of the magnetic field profile during a measurement period; an optical arrangement configured, in use, to introduce light onto the sample portion and to collect light reflected from the sample portion at a plurality of points along the sample path, in order to test the magneto-optical properties of the platter at a plurality of different magnetic fields.

Preferably the magnetic field varies substantially linearly or piece-wise linearly with distance along at least part of the magnetic field profile.

Preferably the magnetic field profile is a four quadrant profile. Preferably the magnetic field varies substantially linearly with distance over each quadrant of the four quadrant profile.

Preferably the magnetic field profile has a triangular waveform.

Preferably the magnetic field profile has a maximum field strength greater than 4 tesla. Preferably the magnetic field profile has a maximum field strength greater than 5 tesla.

Preferably the magnetic field profile has a maximum field strength in the range 4 to 10 tesla.

Preferably the apparatus includes a controller, configured to control the speed of the relative movement in order to define a desired magnetic field ramp as a function of time.

Preferably the controller is configured to control the speed of the relative movement to subject the sample to a magnetic field that varies piece-wise linearly with time.

Preferably the magnetic field profile varies piece-wise linearly with distance and the relative movement is at constant speed.

Preferably the magnetic field ramp varies as one or more cycles of a triangular wave form during a measurement period.

The apparatus may include a user input device, allowing a user to define the desired magnetic field ramp as a function of time, the controller being configured to determine a required speed function for the relative movement in order to provide the desired magnetic field ramp, and to control the speed of the relative movement in accordance with the speed function.

Preferably the speed function defines speed as a function of position along the sample path.

Alternatively the speed function defines speed as a function of time.

Preferably the magnet assembly includes a first pair of magnetic poles with a first pole gap, and the sample path extends through the pole gap.

Preferably the magnet assembly includes a second pair of magnetic poles with a second pole gap, and the sample path extends through the second pole gap.

Preferably the first and second pairs of magnetic poles have opposite polarities.

Preferably the first pole gap is between 5 and 50 mm.

Preferably the second pole gap is between 5 and 50 mm.

Preferably the magnet assembly includes one or more electromagnets. Preferably the electromagnets are superconductor-coiled electromagnets. Preferably the electromagnets are high temperature superconductor-coiled electromagnets.

At least part of the optical arrangement may be arranged in fixed relation to the platter holder.

Alternatively the optical arrangement is arranged in fixed relation to the magnet assembly and provides a plurality of fixed sampling points distributed along the sample path.

Preferably the optical arrangement includes one or more reflectors positioned, in use, within the magnet assembly configured to redirect light onto the sample path.

The optical arrangement may be configured to introduce light onto the one or more reflectors in a direction parallel to the sample path.

Alternatively the optical arrangement is configured to introduce light onto the one or more reflectors from the side of the sample path.

Preferably the optical arrangement includes one or more laser sources.

Preferably the laser sources include one or more laser spots and/or laser stripes.

The optical arrangement may provide a plurality of laser spots distributed along the sample path.

The optical arrangement may provide a plurality of laser spots arranged in a two dimensional matrix.

The optical arrangement may provide one or more laser stripes arranged with their lengths lying along the length of the sample path.

The optical arrangement may provide one or more laser stripes arranged with their lengths lying across the length of the sample path.

Preferably the optical arrangement is configured, in use, to introduce light onto both sides of the platter and to collect light reflected from both sides of the platter, in order to test the magneto-optical properties of both sides of the platter in a single pass.

Preferably the optical arrangement is configured to make magneto-optical Kerr effect measurements.

Preferably the optical arrangement is configured to make polar magneto-optical Kerr effect measurements.

Preferably the apparatus is configured to pass the platter along the sample path repeatedly, the apparatus including a positioning mechanism configured to alter the relative positions of the sample path and either the platter or the platter holder in order to pass a different sample portion along the sample path with each pass.

In a second aspect the invention provides a magneto-optical testing apparatus including: a magnet assembly; a sample path extending through the magnet assembly, a magnetic field produced by the magnet assembly defining a known, varying magnetic field profile along the sample path; a sample holder; a drive arrangement configured to cause relative movement between the magnet assembly and the sample holder, so as to move at least a sample portion of a sample held, in use, by the sample holder along the sampling path to subject the sample portion to at least part of the magnetic field profile such that the sample portion is subjected to a predetermined magnetic field ramp during a measurement period; an optical arrangement configured, in use, to introduce light onto the sample portion and to collect light reflected from the sample portion at a plurality of points along the sample path, in order to test the magneto-optical properties of the sample portion at a plurality of different magnetic fields.

Preferably the magnetic field varies substantially linearly or piece-wise linearly with distance along at least part of the magnetic field profile.

Preferably the magnetic field profile is a four quadrant profile. Preferably the magnetic field varies substantially linearly with distance over each quadrant of the four quadrant profile.

Preferably the magnetic field profile has a triangular waveform.

Preferably the magnetic field profile has a maximum field strength greater than 4 tesla. Preferably the magnetic field profile has a maximum field strength greater than 5 tesla.

Preferably the magnetic field profile has a maximum field strength in the range 4 to 10 tesla.

Preferably the apparatus includes a controller, configured to control the speed of the relative movement in order to define a desired magnetic field ramp as a function of time.

Preferably the controller is configured to control the speed of the relative movement to subject the sample to a magnetic field that varies piece-wise linearly with time.

Preferably the magnetic field profile varies piece-wise linearly with distance and the relative movement is at constant speed.

Preferably the magnetic field ramp varies as one or more cycles of a triangular wave form during a measurement period.

The apparatus may include a user input device, allowing a user to define the desired magnetic field ramp as a function of time, the controller being configured to determine a required speed function for the relative movement in order to provide the desired magnetic field ramp, and to control the speed of the relative movement in accordance with the speed function.

Preferably the speed function defines speed as a function of position along the sample path.

Alternatively the speed function defines speed as a function of time.

Preferably the magnet assembly includes a first pair of magnetic poles with a first pole gap, and the sample path extends through the pole gap.

Preferably the magnet assembly includes a second pair of magnetic poles with a second pole gap, and the sample path extends through the second pole gap.

Preferably the first and second pairs of magnetic poles have opposite polarities.

Preferably the first pole gap is between 5 and 50 mm.

Preferably the second pole gap is between 5 and 50 mm.

Preferably the magnet assembly includes one or more electromagnets. Preferably the electromagnets are superconductor-coiled electromagnets. Preferably the electromagnets are high temperature superconductor-coiled electromagnets.

At least part of the optical arrangement may be arranged in fixed relation to the sample holder.

Alternatively the optical arrangement is arranged in fixed relation to the magnet assembly and provides a plurality of fixed sampling points distributed along the sample path.

Preferably the optical arrangement includes one or more reflectors positioned, in use, within the magnet assembly configured to redirect light onto the sample path.

The optical arrangement may be configured to introduce light onto the one or more reflectors in a direction parallel to the sample path.

Alternatively the optical arrangement is configured to introduce light onto the one or more reflectors from the side of the sample path.

Preferably the optical arrangement includes one or more laser sources.

Preferably the laser sources include one or more laser spots and/or laser stripes.

The optical arrangement may provide a plurality of laser spots distributed along the sample path.

The optical arrangement may provide a plurality of laser spots arranged in a two dimensional matrix.

The optical arrangement may provide one or more laser stripes arranged with their lengths lying along the length of the sample path.

The optical arrangement may provide one or more laser stripes arranged with their lengths lying across the length of the sample path.

Preferably the optical arrangement is configured, in use, to introduce light onto both sides of the sample and to collect light reflected from both sides of the sample, in order to test the magneto-optical properties of both sides of the sample in a single pass.

Preferably the optical arrangement is configured to make magneto-optical Kerr effect measurements.

Preferably the optical arrangement is configured to make polar magneto-optical Kerr effect measurements.

Preferably the apparatus is configured to pass the sample along the sample path repeatedly, the apparatus including a positioning mechanism configured to alter the relative positions of the sample path and either the sample or the sample holder in order to pass a different sample portion along the sample path with each pass.

In a third aspect the invention provides a magnetic testing apparatus including: a magnet assembly; a sample path extending through the magnet assembly, a magnetic field produced by the magnet assembly defining a known, varying magnetic field profile along the sample path; a sample holder; a drive arrangement configured to cause relative movement between the magnet assembly and the sample holder, so as to move at least a sample portion of a sample held, in use, by the sample holder along the sampling path to subject the sample portion to at least part of the magnetic field profile such that the sample portion is subjected to a predetermined magnetic field ramp during a measurement period; a measurement arrangement, configured, in use, to measure one or more properties of the sample portion at a plurality of points along the sample path, in order to test the properties of the sample portion at a plurality of different magnetic fields.

Preferably the magnetic field varies substantially linearly or piece-wise linearly with distance along at least part of the magnetic field profile.

Preferably the magnetic field profile is a four quadrant profile. Preferably the magnetic field varies substantially linearly with distance over each quadrant of the four quadrant profile.

Preferably the magnetic field profile has a triangular waveform.

Preferably the magnetic field profile has a maximum field strength greater than 4 tesla. Preferably the magnetic field profile has a maximum field strength greater than 5 tesla.

Preferably the magnetic field profile has a maximum field strength in the range 4 to 10 tesla.

Preferably the apparatus includes a controller, configured to control the speed of the relative movement in order to define a desired magnetic field ramp as a function of time.

Preferably the controller is configured to control the speed of the relative movement to subject the sample to a magnetic field that varies piece-wise linearly with time.

Preferably the magnetic field profile varies piece-wise linearly with distance and the relative movement is at constant speed.

Preferably the magnetic field ramp varies as one or more cycles of a triangular wave form during a measurement period.

The apparatus may include a user input device, allowing a user to define the desired magnetic field ramp as a function of time, the controller being configured to determine a required speed function for the relative movement in order to provide the desired magnetic field ramp, and to control the speed of the relative movement in accordance with the speed function.

Preferably the speed function defines speed as a function of position along the sample path.

Alternatively the speed function defines speed as a function of time.

Preferably the magnet assembly includes a first pair of magnetic poles with a first pole gap, and the sample path extends through the pole gap.

Preferably the magnet assembly includes a second pair of magnetic poles with a second pole gap, and the sample path extends through the second pole gap.

Preferably the first and second pairs of magnetic poles have opposite polarities.

Preferably the first pole gap is between 5 and 50 mm.

Preferably the second pole gap is between 5 and 50 mm.

Preferably the magnet assembly includes one or more electromagnets. Preferably the electromagnets are superconductor-coiled electromagnets. Preferably the electromagnets are high temperature superconductor-coiled electromagnets.

At least part of the measurement arrangement may be arranged in fixed relation to the sample holder.

Alternatively the measurement arrangement is arranged in fixed relation to the magnet assembly and provides a plurality of fixed sampling points distributed along the sample path.

The measurement arrangement may be an optical arrangement as defined above in relation to the first or second aspect.

Preferably the optical arrangement includes one or more reflectors positioned, in use, within the magnet assembly configured to redirect light onto the sample path.

The optical arrangement may be configured to introduce light onto the one or more reflectors in a direction parallel to the sample path.

Alternatively the optical arrangement is configured to introduce light onto the one or more reflectors from the side of the sample path.

Preferably the optical arrangement includes one or more laser sources.

Preferably the laser sources include one or more laser spots and/or laser stripes.

The optical arrangement may provide a plurality of laser spots distributed along the sample path.

The optical arrangement may provide a plurality of laser spots arranged in a two dimensional matrix.

The optical arrangement may provide one or more laser stripes arranged with their lengths lying along the length of the sample path.

The optical arrangement may provide one or more laser stripes arranged with their lengths lying across the length of the sample path.

Preferably the optical arrangement is configured, in use, to introduce light onto both sides of the sample and to collect light reflected from both sides of the sample, in order to test the magneto-optical properties of both sides of the sample in a single pass.

Preferably the optical arrangement is configured to make magneto-optical Kerr effect measurements.

Preferably the optical arrangement is configured to make polar magneto-optical Kerr effect measurements.

Preferably the apparatus is configured to pass the sample along the sample path repeatedly, the apparatus including a positioning mechanism configured to alter the relative positions of the sample path and either the sample or the sample holder in order to pass a different sample portion along the sample path with each pass.

In a further aspect the invention provides a method of testing a hard disk platter, including: providing a magnet assembly with a sample path extending through the magnet assembly, a magnetic field produced by the magnet assembly defining a known, varying magnetic field profile along the sample path; causing relative movement between the magnet assembly and the platter, so as to move at least a sample portion of the along the sampling path to subject the sample portion to at least part of the magnetic field profile during a measurement period; introducing light onto the sample portion and collecting light reflected from the sample portion at a plurality of points along the sample path, in order to test the magneto-optical properties of the platter at a plurality of different magnetic fields.

In a further aspect the invention provides a method of testing a sample including: providing a magnet assembly with a sample path extending through the magnet assembly, a magnetic field produced by the magnet assembly defining a known, varying magnetic field profile along the sample path; causing relative movement between the magnet assembly and a sample, so as to move at least a sample portion of the sample along the sampling path to subject the sample portion to at least part of the magnetic field profile such that the sample portion is subjected to a predetermined magnetic field ramp or magnetic field profile during a measurement period; introducing light onto the sample portion and collecting light reflected from the sample portion at a plurality of points along the sample path, in order to test the magneto-optical properties of the sample portion at a plurality of different magnetic fields.

In a further aspect the invention provides a method of testing a sample including: providing a magnet assembly with a sample path extending through the magnet assembly, a magnetic field produced by the magnet assembly defining a known, varying magnetic field profile along the sample path; causing relative movement between the magnet assembly and a sample, so as to move at least a sample portion of the sample along the sampling path to subject the sample portion to at least part of the magnetic field profile such that the sample portion is subjected to a predetermined magnetic field ramp or magnetic field profile during a measurement period; measuring one or more properties of the sample portion at a plurality of points along the sample path, in order to test the properties of the sample portion at a plurality of different magnetic fields.

In this specification the term "profile" refers to a function of distance. For example, the "magnetic field profile" is the magnetic field as a function of distance. The term "ramp" refers to a function of time. For example, the "magnetic field ramp" is the magnetic field to which a sample point is subjected, as a function of time. The term "quadrant" refers to a magnetic field quadrant that changes between 0 and either a maximum or a minimum field. For example, a magnetic field changing from 0 to $B_{max}$ defines one quadrant (where $B_{max}$ is a maximum magnetic field). A magnetic field changing from $B_{max}$ to 0 defines another quadrant. A four quadrant scan involves a magnetic field that changes through a full cycle, for example from 0 to $B_{max}$, $B_{max}$ to 0, 0 to $B_{min}$, $B_{min}$ to 0 (where $B_{min}$ is a minimum magnetic field). The terms "four quadrant profile" and "four quadrant ramp" have corresponding meanings. The term "high temperature superconductor" means a superconductor with transition temperature above 30 K and preferably above 77 K.

BRIEF DESCRIPTION OF THE DRAWINGS

The invention will now be described by way of example only, with reference to the accompanying drawings, in which:

FIG. 16 is a schematic end view of a testing apparatus according to another embodiment.

DETAILED DESCRIPTION

Figure 1:
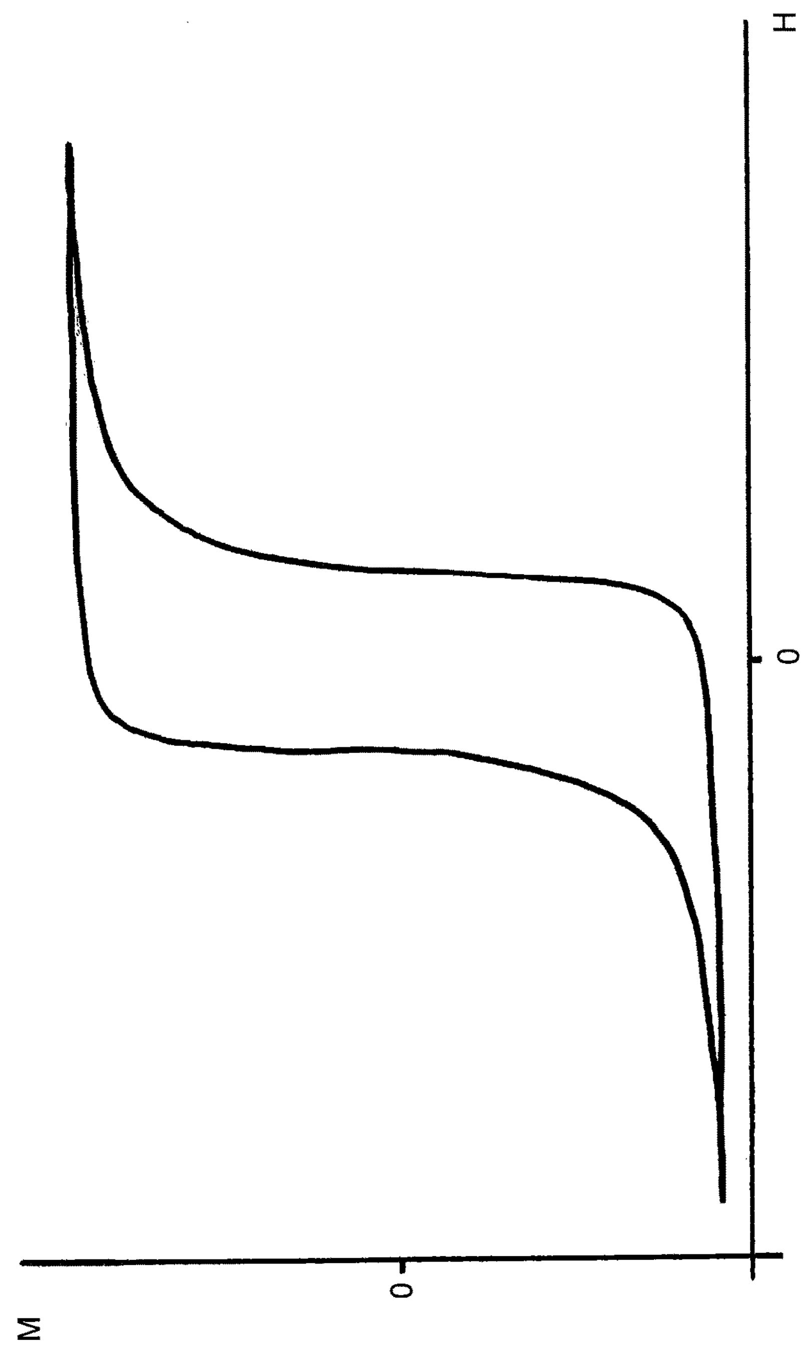
FIG. 1 shows a hysteresis loop from a prior art MOKE experiment.
Figure 2:
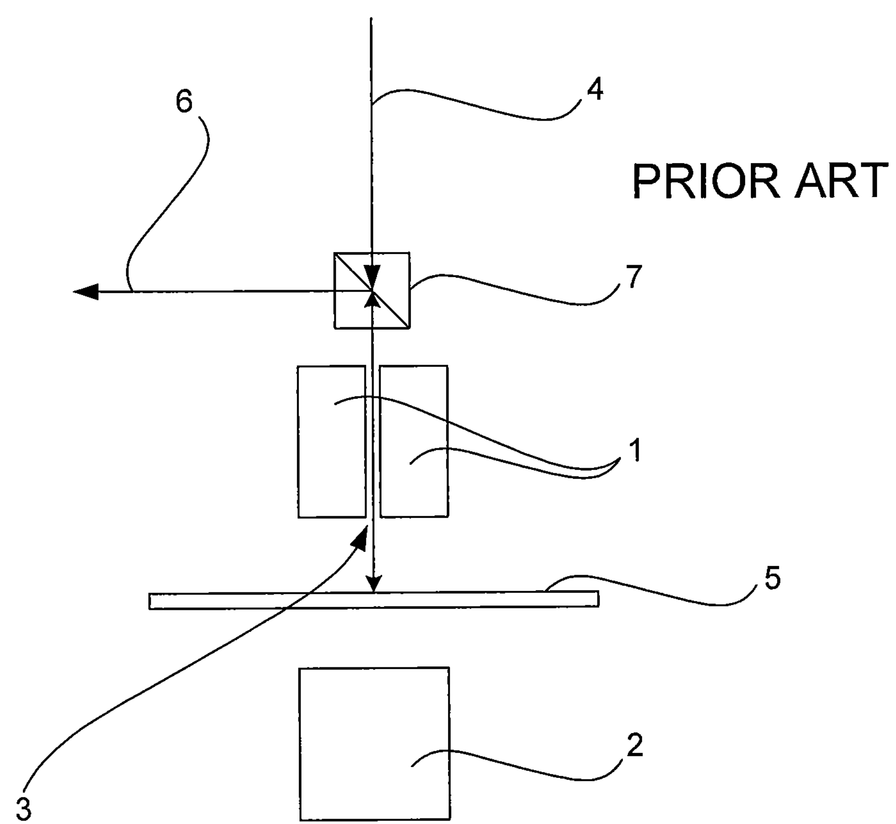
FIG. 2 shows a prior art MOKE apparatus.
Figure 3:
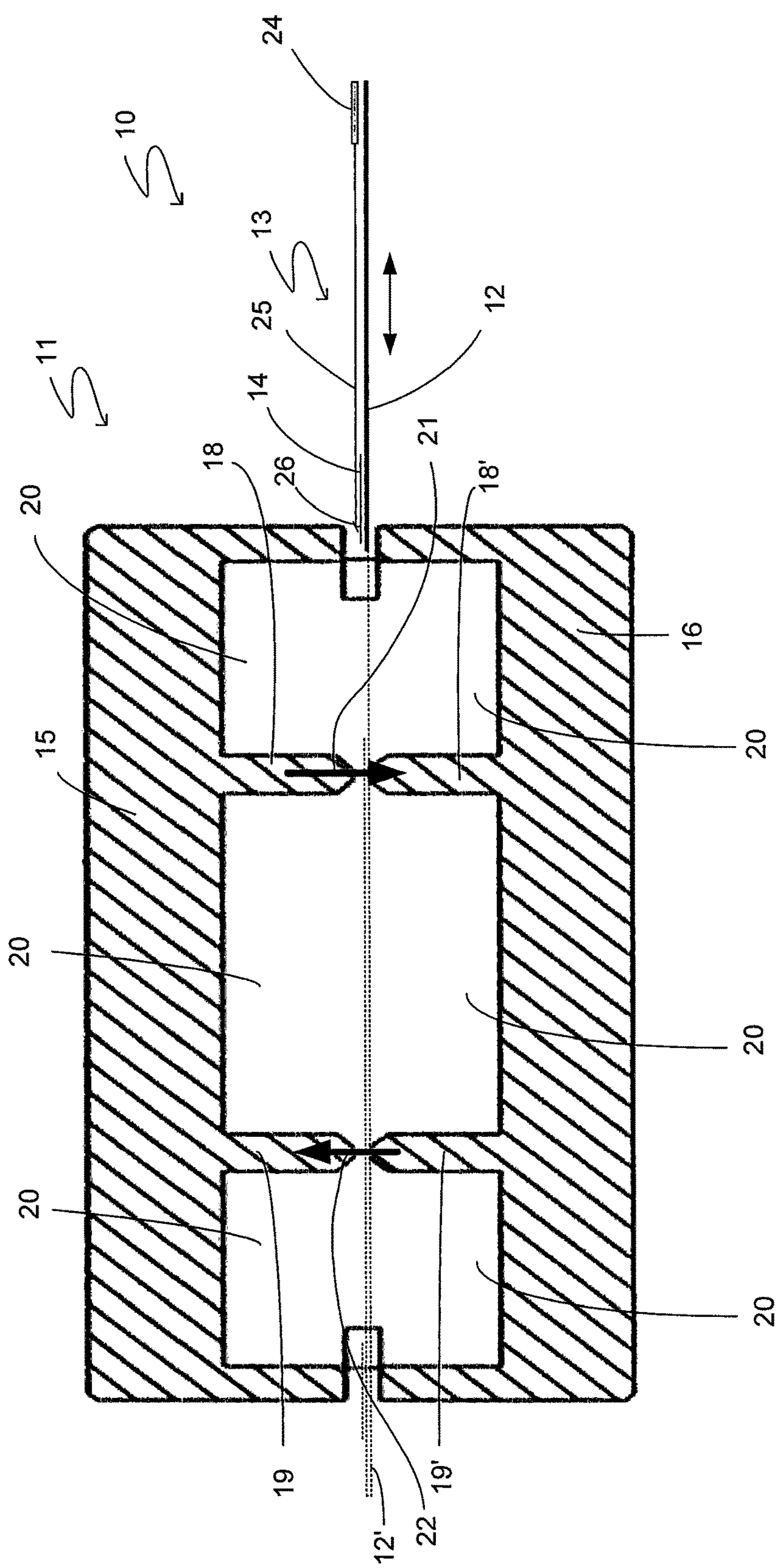
FIG. 3 is a schematic diagram showing a testing apparatus according to one embodiment.

FIG. 3 is a schematic diagram of a testing apparatus 10 according to one embodiment. The apparatus 10 includes a magnet assembly 11, sample holder 12 and optical arrangement 13. A sample 14 is shown mounted on the sample holder 12.

The magnet assembly 11 includes an upper portion 15 and a lower portion 16, which include first magnetic poles 18, 18' and second magnetic poles 19, 19'. As shown in FIG. 3, each pole extends from a base into a central region, and is surrounded by a space 20 in which electromagnet coils (not shown in FIG. 3) are arranged.

The magnet assembly is operated at fixed current. This means that the magnetic field within the magnet assembly is constant, or static, over time.

The first magnetic poles 18, 18' may define a region 21 of minimum magnetic field ($B_{min}$). The second magnetic poles 19, 19' may have opposite polarity to the first magnetic poles 18, 18', in which case they will define a region 22 of maximum magnetic field ($B_{max}$). The first and second magnetic poles may have substantially equal strength, in which case $B_{min}=-B_{max}$.

The sample holder 12 is configured to move through the magnet assembly 11 in order to move the sample 14 through the varying magnetic field provided by the magnet assembly. The sample holder may move to the position 12' indicated in dashed line. In other words, the sample 14 is moved along a sample path that extends through the magnet assembly 11.

Figure 4:
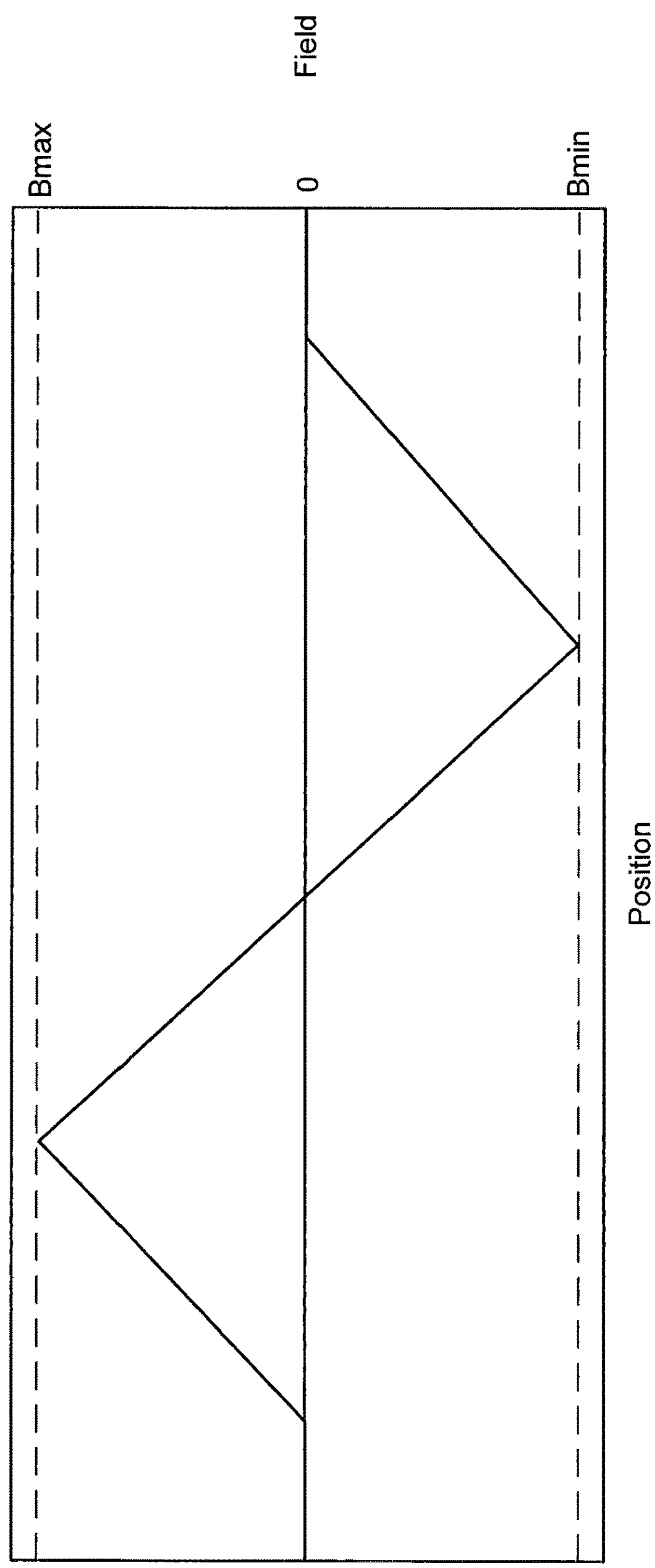
FIG. 4 is a graph showing an ideal magnetic field profile for the apparatus of FIG. 3.

FIG. 4 is an ideal magnetic field profile provided by the magnet assembly 11 along the sample path. This graph shows the magnetic field on the sample path as a function of position or distance. The field outside the magnet assembly is substantially zero. Inside the magnetic assembly the field has a substantially linear profile in each quadrant, defining a triangular waveform. The field extends though all four quadrants, providing a four quadrant magnetic field profile. Measurements may be made over the entire four quadrants of magnetic field profile, or over only a part of the field profile (e.g. over one quadrant, two or three quadrants or some other part of the profile). Further, other magnetic field profiles, such as non-linear profiles or even asymmetric profiles, may be suitable for some applications.

Measurements may also be made over any desired magnetisation loops. For example, part of the magnetic field profile may be utilised more than once, or more than other parts of the profile. For example, one may want to cycle back and forth within one quadrant before continuing on the full four quadrant profile. One may also want to demagnetise a sample by cycling between successively decreasing values of Hmin and Hmax. These and other methods are possible by appropriate movement of the sample along the field profile.

Figure 3A:
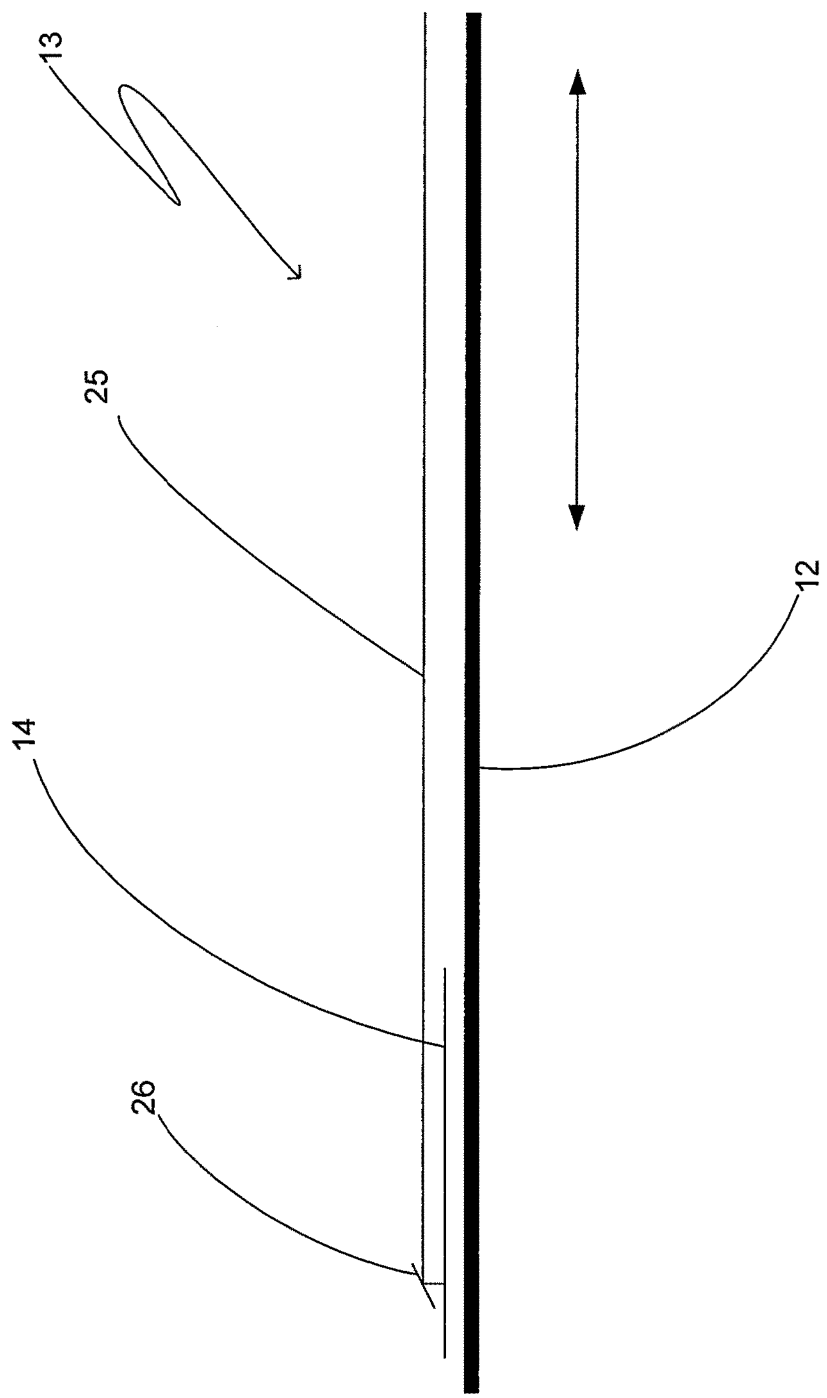
FIG. 3A is an expanded view of part of FIG. 3.

The optical arrangement 13 includes a laser source 24. The laser beam 25 travels towards the sample 14 and is reflected by a reflector 26 onto the sample 14. FIG. 3A is an expanded view of this arrangement, showing the reflector and sample positions in greater detail.

In this configuration, the laser beam strikes the sample substantially perpendicular to the sample surface. The reflected beam is redirected by the reflector 26 back down the path of the incoming laser beam 25 and may be separated by suitable optical components such as a beamsplitter. Various further optical components are also used, as will be understood by the skilled reader. In particular, a light source, light detector, polariser, analyser, modulator, lenses etc may be used as necessary for the particular application.

This arrangement may be used in order to conduct polar MOKE measurements. The optical arrangement defines a single point on the sample where the laser beam is reflected. Optical measurements may be made either periodically or continuously as the sample is moved along the sample path through the magnet assembly.

The magnetic field profile varies over distance, so that as the sample is moved along the sample path (and therefore along the magnetic field profile shown in FIG. 4), it is subjected to a magnetic field ramp, i.e. a magnetic field that varies over time. The magnetic field ramp depends on the magnetic field profile and on the speed of movement of the sample.

If the speed at which the sample is moved along the sample path is constant, then the magnetic field ramp will have the same shape as the magnetic field profile. That is, for the profile of FIG. 4 the magnetic field ramp (field as a function of time) will have a generally triangular waveform.

However, in some embodiments, the shape of the magnetic field ramp is not necessarily the same as the shape of the magnetic field profile. In those embodiments the speed of sample movement is controlled in order to convert the profile into a desired magnetic field ramp. Various ramp shapes may be desirable, depending on the application. The Applicant's system is capable of providing various ramp shapes, including sawtooth or sinusoidal shapes, or other desired shapes.

The apparatus may include a controller that is configured to control the movement of the sample holder. Further, the controller may receive user input of a desired magnetic field ramp, determine the speed function that will deliver that ramp and control the movement speed accordingly.

Figure 5:
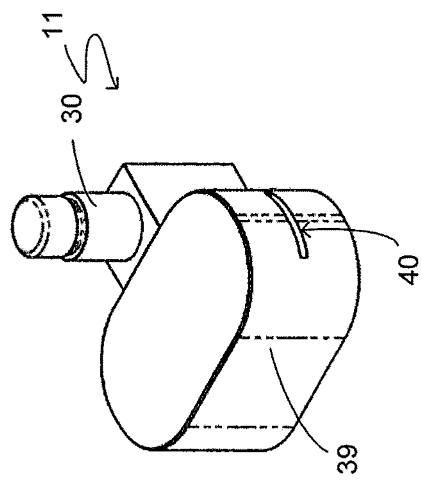
FIG. 5 is a perspective view of a magnet assembly according to a further embodiment.
Figure 6:
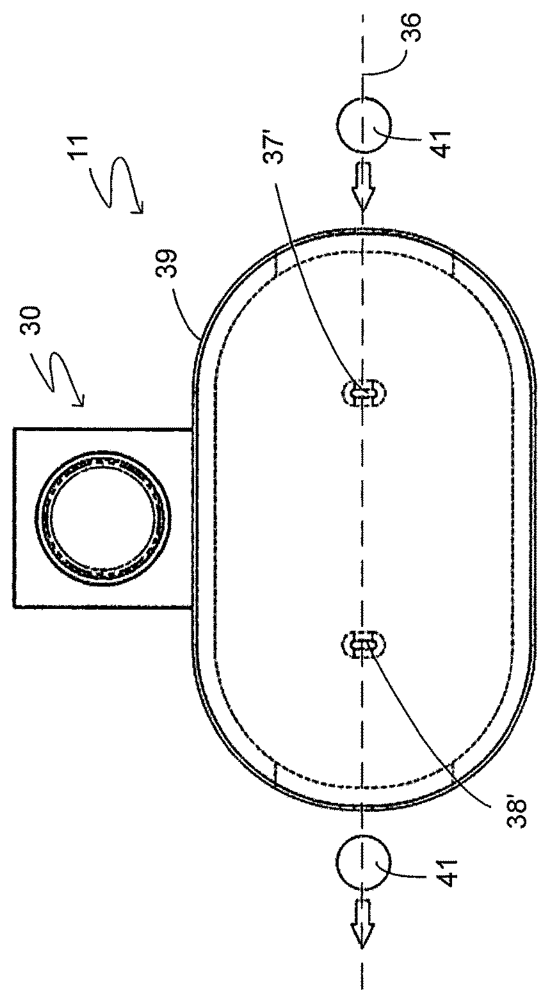
FIG. 6 is a cut away top view of the magnet assembly of FIG. 5, showing the internal magnetic poles.
Figure 7:
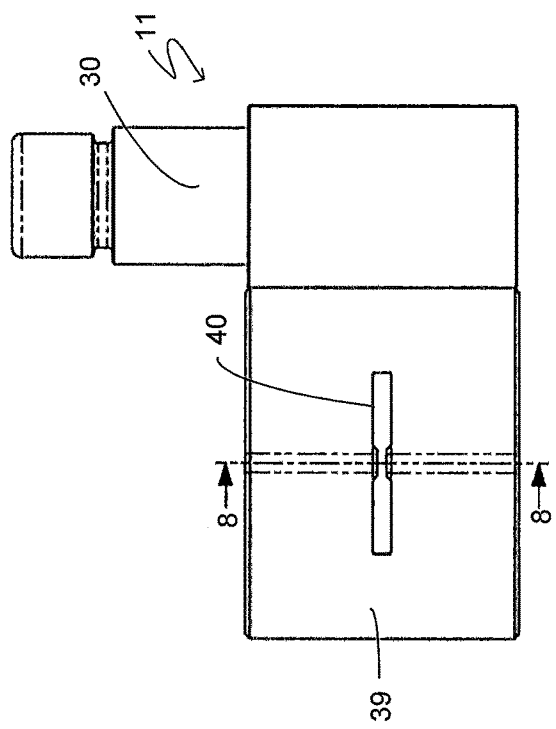
FIG. 7 is an end view of the magnet assembly of FIG. 5.
Figure 8:
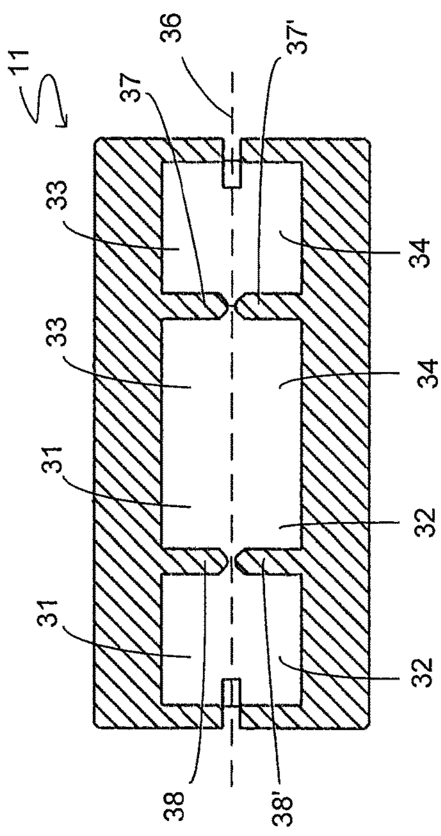
FIG. 8 is a cross-section along the line 8-8 in FIG. 7.

FIGS. 5 to 8 show a magnet assembly 11 according to a further embodiment. This may form part of an apparatus that is particularly suited to measurement of hard disk platters. FIG. 5 is a perspective view; FIG. 6 is a cut away top view, showing the internal magnetic poles; FIG. 7 is an end view; and FIG. 8 is a cross-section along the line 8-8 in FIG. 7.

In this embodiment the magnet assembly includes high temperature superconductor-coiled electromagnets. The magnet assembly 11 therefore includes a cooling system 30 (such as a helium gas cooling system) configured to lower the temperature of the superconducting wire below its transition temperature. Suitable high temperature superconducting materials include Bismuth-Strontium-Calcium-Copper-Oxide family of superconductors known in the art, and the rare-earth-Barium-Copper-Oxide family of superconductors known in the art.

However, in other embodiments other types of magnet may be used. Copper-coiled magnets may provide acceptable performance up to magnetic fields of about 4 to 5 tesla.

Low temperature superconductor-coiled magnets may be used, but require more expensive cooling systems due to the lower temperatures required.

Newer families of superconductors, such as $MgB_2$, may be used as they become available.

Figure 8A:
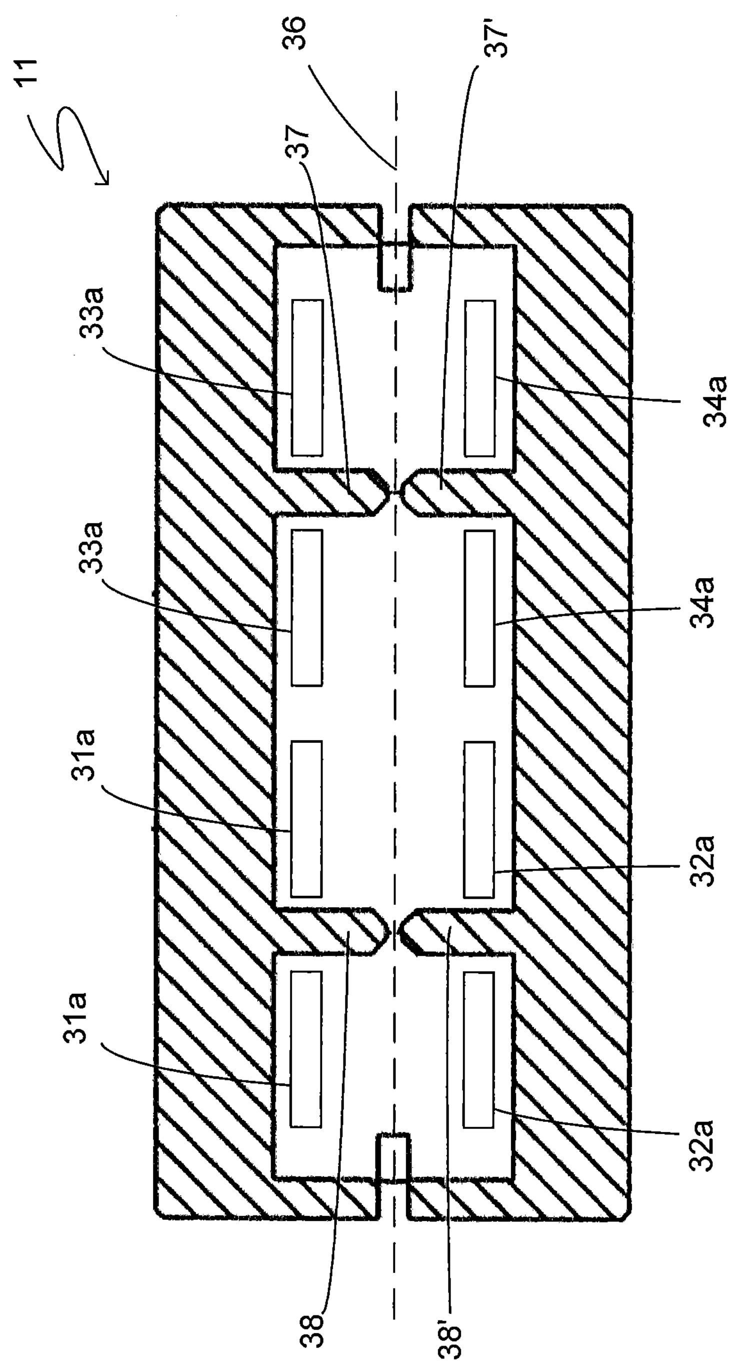
FIG. 8A is a similar view to FIG. 8, showing the positions of electromagnet coils.

The cross-sectional structure shown in FIG. 8 is generally similar to that of FIG. 3, and the superconducting coils (not shown in FIG. 8) will lie in the regions 31, 32, 33, 34. FIG. 8A shows the positions of coils 31*a*, 32*a*, 33*a* and 34*a*.

The magnetic poles or yokes may be formed from any suitable material, including any magnet iron, low carbon steel or other material such as iron-cobalt alloys including Permendur as known in the art.

A sample path 36 extends through the magnet assembly, between the first magnetic poles 37, 37' and the second magnetic poles 38, 38'. As shown in FIGS. 5 and 7, the housing 39 of the magnet assembly 11 may be provided with an entrance opening 40. The sample may be introduced into the magnet assembly through the entrance opening and moved along the sample path 36. The sample may be withdrawn through the entrance opening 40, or may exit through an exit opening provided at the other end of the magnet assembly 11.

In this embodiment the maximum field may be around 7 tesla. The pole gap may be around 5 to 50 mm but could be larger if necessary for the application. The pole-pole separation (i.e. the distance between the two sets of poles along the sample path) may be around 300 mm. The length of the sample path for a full four quadrant cycle may be around 700 mm. The cycle time may be around 10-30 seconds, or faster with faster linear motion.

Figure 9:
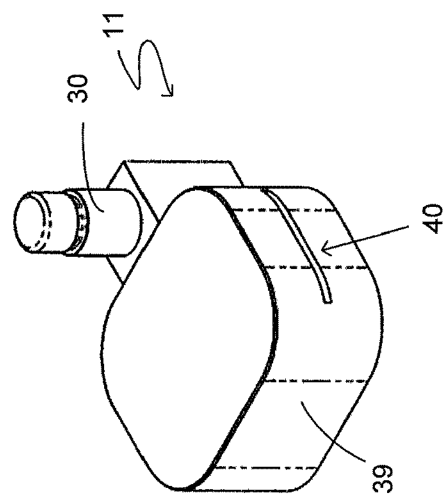
FIG. 9 is a perspective view of a magnet assembly according to another embodiment.
Figure 10:
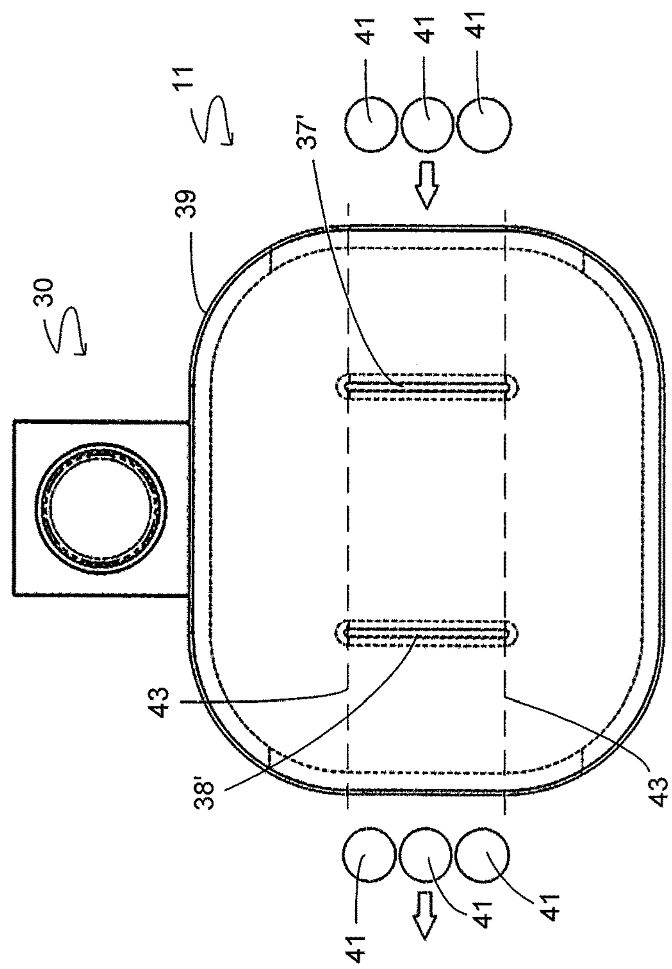
FIG. 10 is a cut away top view of the magnet assembly of FIG. 9, showing the internal magnetic poles.
Figure 11:
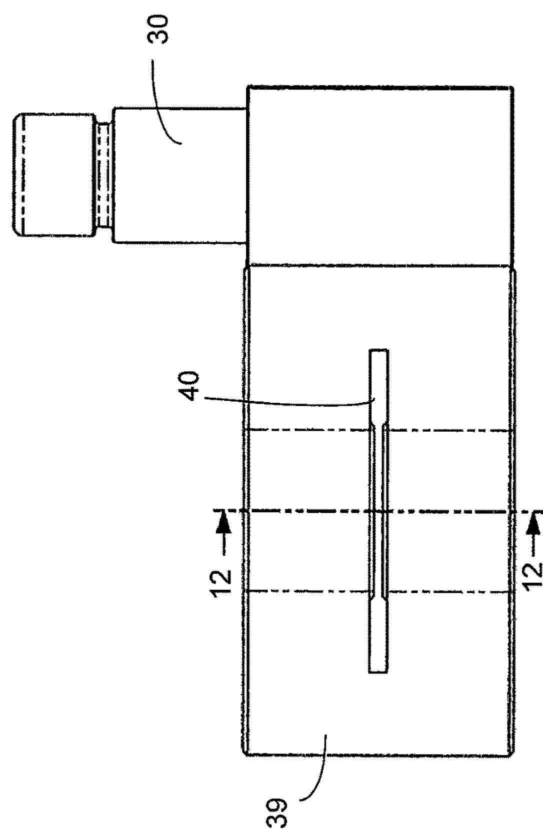
FIG. 11 is an end view of the magnet assembly of FIG. 9.
Figure 12:
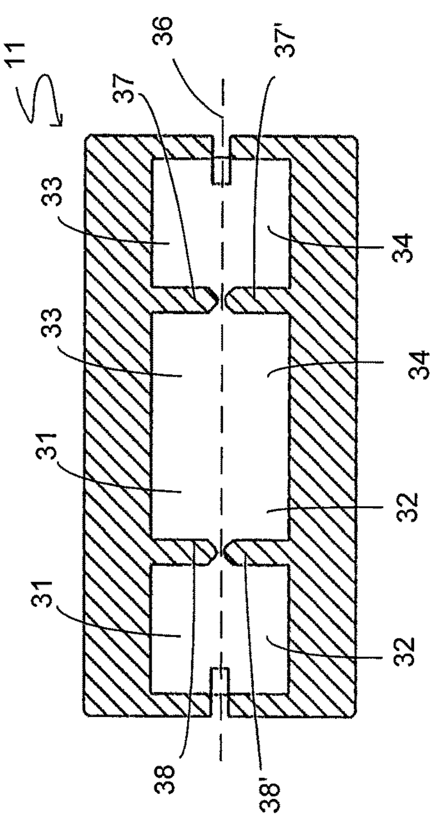
FIG. 12 is a cross-section along the line 12-12 in FIG. 11.

FIGS. 9 to 12 show a magnet assembly 11 according to another embodiment. This may also form part of an apparatus that is particularly suited to measurement of hard disk platters. FIG. 9 is a perspective view; FIG. 10 is a cut away top view, showing the internal magnetic poles; FIG. 11 is an end view; and FIG. 12 is a cross-section along the line 12-12 in FIG. 11.

This magnet assembly is generally similar to that of FIGS. 5 to 8. However, in this embodiment the magnetic poles 37, 37', 38, 38' are wider, as shown in FIG. 10. This width allows larger samples 41, or (as shown in FIG. 10) multiple samples 41 to be moved along a broad sample path (between dashed lines 43) in a single pass. The entrance and exit openings are also widened accordingly.

Figure 13:
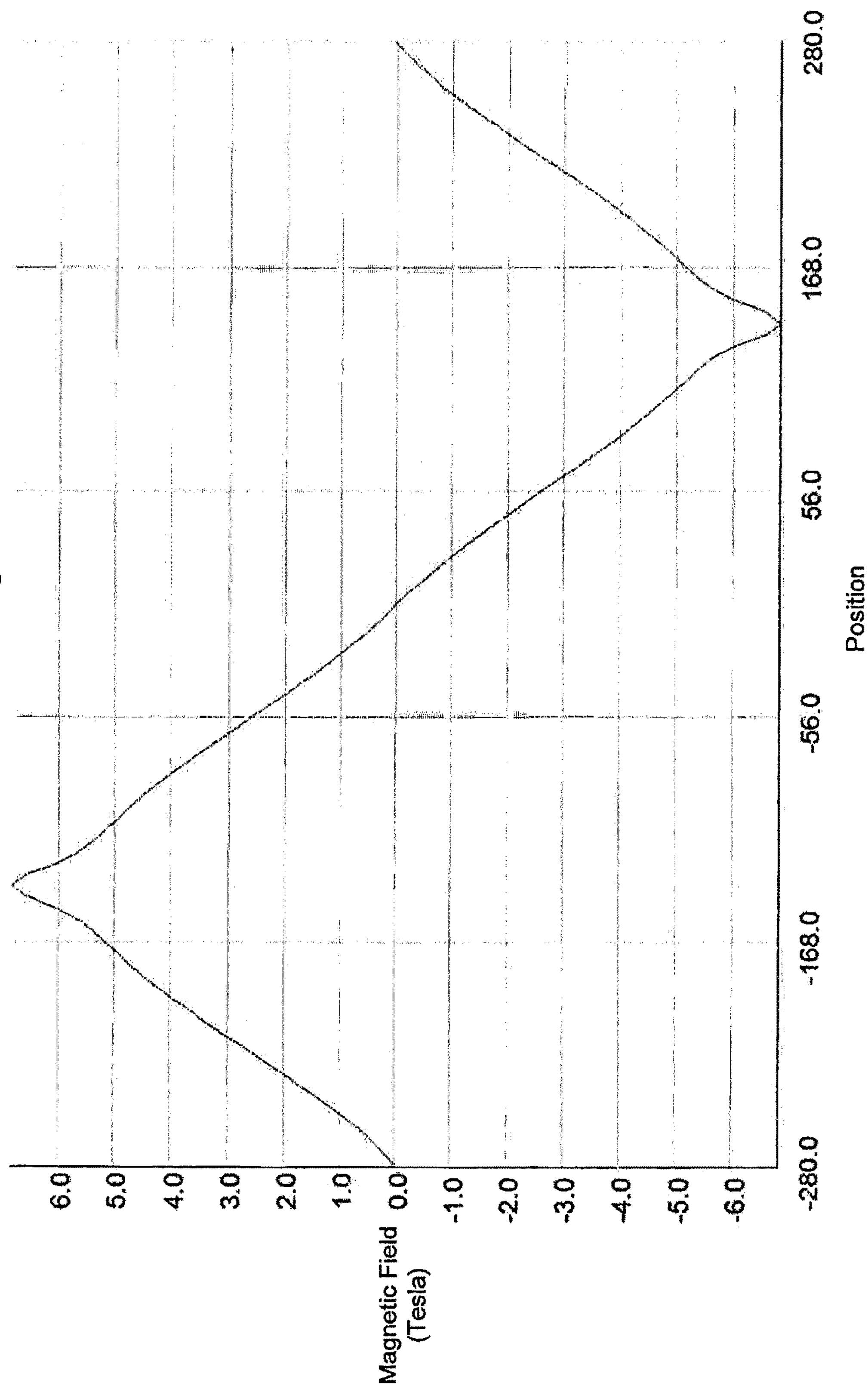
FIG. 13 is a graph showing the magnetic field profile through the magnet assembly of FIG. 5.

FIG. 13 is a graph produced by a model of the magnet assembly in FIGS. 5 to 8. This graph shows a magnetic field profile that is substantially piece-wise linear and close to the ideal profile shown in FIG. 4. The linearity of field gradient may be better than around 5% variance from linear.

The magnet assembly of either FIGS. 5 to 8, or of FIGS. 9 to 12, may be combined with any suitable measurement arrangement designed to measure magnetic properties of the samples. In preferred embodiments the measurement arrangement is an optical arrangement configured to measure magneto-optical properties (such as MOKE properties) as the sample moves along the magnetic profile. The optical arrangement may be similar to that shown in FIG. 3, with the laser beam or other light source introduced through the entrance opening and at least part of the optical arrangement (i.e. at least the reflector) moving with the sample through the magnet assembly.

Figure 14:
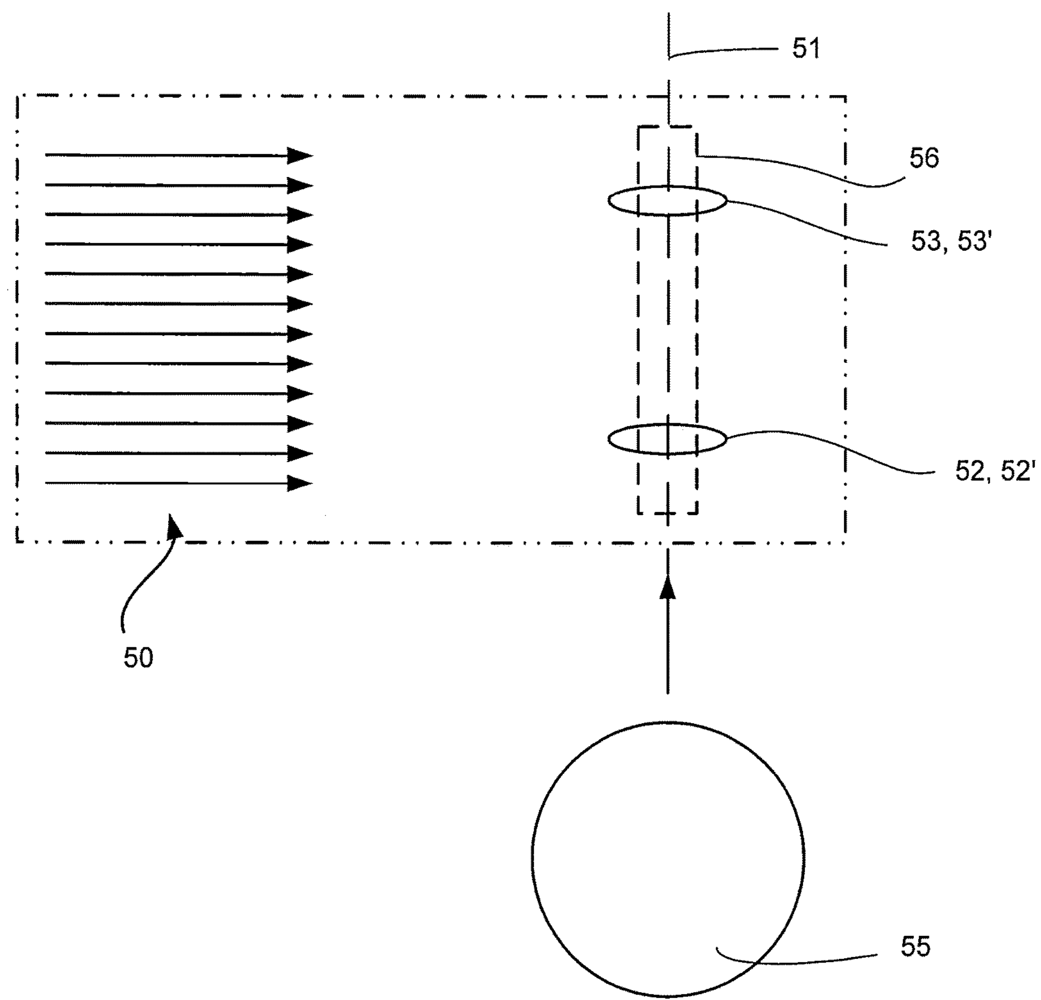
FIG. 14 is a schematic top view of a testing apparatus according to a further embodiment.
Figure 15:
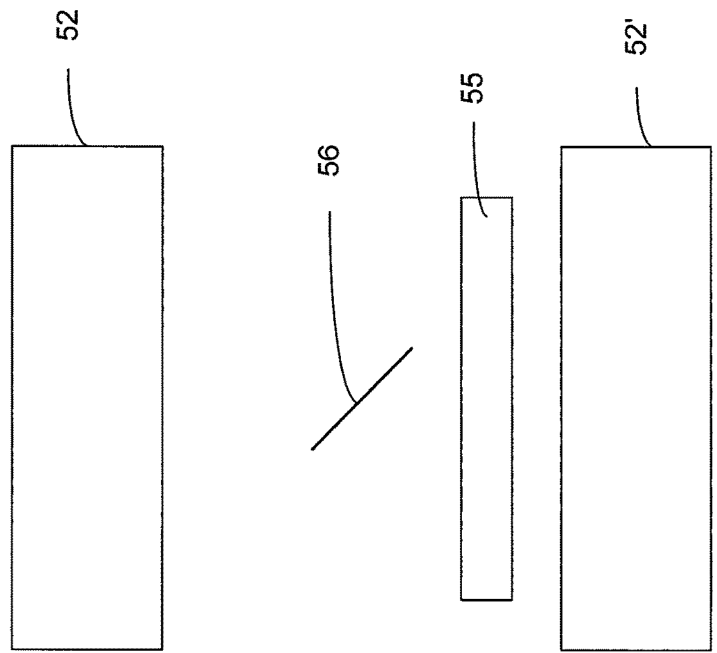
FIG. 15 is a schematic end view of the apparatus of FIG. 14.

FIG. 14 is a schematic top view and FIG. 15 is a schematic end view showing an alternative optical arrangement. In this embodiment the optical arrangement is fixed with respect to the magnet assembly 11, while the sample moves through the magnet assembly.

The optical arrangement includes multiple laser or other light sources configured to produce parallel laser or light beams 50 that are positioned to one side of, and directed towards, the sample path 51. Alternatively the multiple laser sources may be replaced by a smaller number of sources configured to produce laser stripes. The sample path 51 extends between magnet poles 52, 52', 53, 53' as in earlier described embodiments. The sample 55 is moved along the sample path 51 through the magnetic assembly. In this embodiment either a long mirror 56 or a number of mirrors is/are arranged at an angle above the sample path in order to redirect the laser beams 50 down onto the sample path. Light reflected by the sample will travel back along the same path and be separated as before.

The use of either laser stripes striking the sample parallel to the sample path, or multiple laser spots arranged along the length of the sample path, allows multiple points on the sample to be measured in a single pass. Each sample point passes along the sample path and is measured at multiple positions along the length of the sample path.

FIG. 16 is a schematic end view of a further embodiment. This embodiment is similar to that of FIGS. 14 and 15, but the single set of laser beams (or laser stripe) of FIGS. 14 and 15 is replaced by several banks 60 of laser beams. Each bank of laser beams is similar to beams of FIG. 14, and may be composed of multiple beams or one or more stripes.

The Applicant's system does not necessarily require a laser, or a small diameter beam. The system is not constrained by the small hole usually present in prior MOKE apparatus, so there is no need for a small diameter collimated beam. In some embodiments broad area beams (1 $cm^2$ for example) may be used to measure large sample regions. Such a measurement may provide an average reading over a larger surface area.

The presence of a mirror in a region of the optical path exposed to a significant magnetic field does have an effect on the MOKE measurements. However, corrections can be made to cater for these. One correction method is described in Arora et al (Arora, Ghosh and Sugunakar "*A mirror based polar magneto-optical Kerr effect spectroscopy arrangement*" Review of Scientific Instruments 82 123903 (2011)), the entire contents of which are hereby incorporated by reference herein.

The Applicant's magnet assembly and measurement arrangement may be employed for any measurement requiring a magnetic field ramp. These may include electrical, optical or other measurements. In preferred embodiments the apparatus is suitable for magneto-optical measurements, in particular MOKE measurements. The apparatus may be adapted for polar, transverse or longitudinal MOKE measurements. However, for many applications polar MOKE measurements are preferred.

The magnetic field profile is fixed during the measurement period. However, the profile may be adjustable for different measurements (e.g. by selection of the current level) such that different profiles may be obtained for different measurements.

As the magnetic field profile is fixed during the measurement period, the measurement period is governed by the speed of sample movement. In one embodiment a 7 tesla four-quadrant field cycle measurement could be carried out in less than 30 seconds at a transport speed as slow as 3 cm/s. Cycle time could be reduced to 10 seconds by increasing the transport speed to 10 cm/s.

Due to these much faster measurement speeds the Applicant's system is suitable for many applications, such as quality assurance testing in a production environment, for which existing technology is too slow.

In addition to the faster speed of each measurement pass, multiple sample spots may be measured with each pass (for example using one of the optical arrangements discussed above). This further increases the speed of data capture. Further, a positioning mechanism may be provided to alter the relative positions of the sample path and either the platter or the platter holder in order to measure a different sample portion with each pass. In one minute six such passes could be made at 10 seconds per pass.

Although the Applicant's apparatus has been described as requiring movement of a sample through a magnet assembly, some embodiments could use movement of the magnet assembly with respect to a stationary sample. At a broad level, what is required is relative movement of the sample and magnet assembly.

The system has been described above as a one sided measurement system, i.e. for making measurements on one side of a sample. However, by replicating the optics described above it is possible to make measurements on both sides of the sample (i.e. both top and bottom surfaces) in a single pass. This is particularly advantageous for materials with two active surfaces, for example two sided hard disk platters.

The applicant's apparatus may be adapted to test any desired sample. In preferred embodiments the apparatus is configured to test hard disk platters.

The Applicant's system provides a magnetic field ramp that is provided by a fixed current magnet assembly and relative movement of the sample and magnet assembly. The use of fixed current magnets reduces heat production and inefficiency in the magnet coils, particularly where superconductor-coiled magnets are used. This reduces costs and cooling requirements. Further, in a fixed current system, in the absence of these heating effects, the coils can operate at higher current density and therefore less wire is required, providing an important cost advantage. The fixed current magnets also produce reduced eddy currents, improving performance.

As noted above, the avoidance of these problems also avoids the need for the slow ramp speeds associated with electrical ramping and provides faster measurement.

A further advantage is that fringe fields produced by the fixed current magnets are static and their effects on nearby equipment can therefore be more easily compensated for than is the case for varying fields.

The light source used may be a laser source, or any other suitable light source.

The Applicant's apparatus has been described above with reference to a magnet assembly including two coils and a yoke with two magnetisable poles, each separated by a pole gap. This is advantageous because it defines a full four quadrant field profile.

However, in other embodiments a different number of pairs of magnetic poles may be used. For example, for some embodiments a single pair of poles may be used. In other embodiments three pairs of poles may be used.

Further, other types of magnet may be used. For example, a split pair of solenoids may be used to define a pair of magnetic poles with a pole gap between them, with or without yoke and poles, and with the possibility of transporting the sample in and out of the high field region. The sample may be flipped upside down and the transport repeated to provide the opposite field polarity.

While the present invention has been illustrated by the description of the embodiments thereof, and while the embodiments have been described in detail, it is not the intention of the Applicant to restrict or in any way limit the scope of the appended claims to such detail. Further, the above embodiments may be implemented individually, or may be combined where compatible. Additional advantages and modifications, including combinations of the above embodiments, will readily appear to those skilled in the art. Therefore, the invention in its broader aspects is not limited to the specific details, representative apparatus and methods, and illustrative examples shown and described. Accordingly, departures may be made from such details without departure from the spirit or scope of the Applicant's general inventive concept.

The invention claimed is:

1. A magneto-optical hard disk platter testing apparatus, including:

i. a magnet assembly comprising at least two pairs of magnetic poles;

ii. a sample path extending through the magnet assembly, a magnetic field produced by the magnet assembly defining a known, varying magnetic field profile along the sample path;

iii. a platter holder;

iv. a drive arrangement configured to cause application of the known, varying magnetic field profile to the sample portion by causing relative movement between the magnet assembly and the platter holder, so as to move at least a sample portion of a platter held, in use, by the platter holder along the sample path to subject the sample portion to the known, varying magnetic field profile during a measurement period;

v. an optical arrangement configured, in use, to introduce light onto the sample portion and to collect light reflected from the sample portion at a plurality of points along the sample path, in order to test the magneto-optical properties of the platter at a plurality of different magnetic fields.

2. A magneto-optical testing apparatus including:

i. a magnet assembly comprising at least one pair of magnetic poles with a pole gap;

ii. a sample path extending through the magnet assembly, a magnetic field produced by the magnet assembly defining a known, varying magnetic field profile along the sample path, wherein the sample path extends through the pole gap of the magnet assembly;

iii. a sample holder;

iv. a drive arrangement configured to cause application of the known, varying magnetic field profile to the sample portion by causing relative movement between the magnet assembly and the sample holder, so as to move at least a sample portion of a sample held, in use, by the sample holder along the sample path and through the pole gap to subject the sample portion to the known, varying magnetic field profile such that the sample portion is subjected to a predetermined magnetic field ramp or magnetic field profile during a measurement period;

v. an optical arrangement configured, in use, to introduce light onto the sample portion and to collect light reflected from the sample portion at a plurality of points along the sample path, in order to test the magneto-optical properties of the sample portion at a plurality of different magnetic fields.

3. An apparatus as claimed in claim 2 wherein at least part of the optical arrangement is arranged in fixed relation to the sample holder.

4. An apparatus as claimed in claim 2 wherein the optical arrangement is arranged in fixed relation to the magnet assembly and provides a plurality of fixed sampling points distributed along the sample path.

5. An apparatus as claimed in claim 2 wherein the optical arrangement includes one or more reflectors positioned, in use, within the magnet assembly configured to redirect light onto the sample path.

6. An apparatus as claimed in claim 2 wherein the optical arrangement includes one or more laser sources.

7. An apparatus as claimed in claim 6 wherein the laser sources include one or more laser spots and/or laser stripes.

8. An apparatus as claimed in claim 7 wherein the optical arrangement provides a plurality of laser spots distributed along the sample path.

9. An apparatus as claimed in claim 2 wherein the optical arrangement is configured, in use, to introduce light onto both sides of the sample and to collect light reflected from both sides of the sample, in order to test the magneto-optical properties of both sides of the sample in a single pass.

10. An apparatus as claimed in claim 2 wherein the optical arrangement is configured to make magneto-optical Kerr effect measurements.

11. An apparatus as claimed in claim 10 wherein the optical arrangement is configured to make polar magneto-optical Kerr effect measurements.

12. A magnetic testing apparatus including:

i. a magnet assembly comprising a first pair of magnetic poles with a first pole gap and a second pair of magnetic poles with a second pole gap;

ii. a sample path extending through the magnet assembly, a magnetic field produced by the magnet assembly defining a known, varying magnetic field profile along the sample path;

iii. a sample holder;

iv. a drive arrangement configured to cause application of the known, varying magnetic field profile to the sample portion by causing relative movement between the magnet assembly and the sample holder, so as to move at least a sample portion of a sample held, in use, by the sample holder along the sample path and through the first pole gap and the second pole gap to subject the sample portion to the known, varying magnetic field profile such that the sample portion is subjected to a predetermined magnetic field ramp or magnetic field profile during a measurement period;

v. a measurement arrangement, configured, in use, to measure one or more properties of the sample portion at a plurality of points along the sample path, in order to test the properties of the sample portion at a plurality of different magnetic fields.

13. An apparatus as claimed in claim 12 wherein the magnetic field varies substantially linearly or piece-wise linearly with distance along at least part of the magnetic field profile.

14. An apparatus as claimed in claim 12 wherein the magnetic field profile is a four quadrant profile.

15. An apparatus as claimed in claim 14 wherein the magnetic field varies substantially linearly with distance over each quadrant of the four quadrant profile.

16. An apparatus as claimed in claim 12 wherein the magnetic field profile has a maximum field strength in the range 4 to 10 tesla.

17. An apparatus as claimed in claim 12 including a controller, configured to control the speed of the relative movement in order to define a desired magnetic field ramp as a function of time.

18. An apparatus as claimed in claim 17 wherein the controller is configured to control the speed of the relative movement to subject the sample to a magnetic field that varies piece-wise linearly with time.

19. An apparatus as claimed in claim 18 wherein the magnetic field ramp varies as one or more cycles of a triangular wave form during a measurement period.

20. An apparatus as claimed in claim 17, further including a user input device, allowing a user to define the desired magnetic field ramp as a function of time, the controller being configured to determine a required speed function for the relative movement in order to provide the desired magnetic field ramp, and to control the speed of the relative movement in accordance with the speed function.

21. An apparatus as claimed in 12 wherein the first and second pairs of magnetic poles have opposite polarities.

22. An apparatus as claimed in claim 12 wherein the first pole gap and the second pole gap are each between 5 and 50 mm.

23. An apparatus as claimed in claim 12 wherein the magnet assembly includes one or more electromagnets.

24. An apparatus as claimed in claim 23 wherein the electromagnets are high temperature superconductor-coiled electromagnets.

25. An apparatus as claimed in claim 12 wherein at least part of the measurement arrangement is arranged in fixed relation to the sample holder.

26. An apparatus as claimed in claim 12 wherein the measurement arrangement is arranged in fixed relation to the magnet assembly and provides a plurality of fixed sampling points distributed along the sample path.

27. An apparatus as claimed in claim 12 configured to pass the sample along the sample path repeatedly, the apparatus including a positioning mechanism configured to alter the relative positions of the sample path and either the sample or the sample holder in order to pass a different sample portion along the sample path with each pass.

* * * * *